US006323209B1

(12) United States Patent
Frost

(10) Patent No.: US 6,323,209 B1
(45) Date of Patent: Nov. 27, 2001

(54) METHOD OF TREATING OR INHIBITING COLONIC POLYPS

(75) Inventor: Philip Frost, Morris Township, NJ (US)

(73) Assignee: American Cyanamid Company, Madison, NJ (US)

( * ) Notice: Subject to any disclaimer, the term of this patent is extended or adjusted under 35 U.S.C. 154(b) by 0 days.

(21) Appl. No.: 09/185,066

(22) Filed: Nov. 3, 1998

Related U.S. Application Data

(60) Provisional application No. 60/112,025, filed on Nov. 6, 1997.

(51) Int. Cl.$^7$ .................................................. A61K 31/505
(52) U.S. Cl. ............................................ 514/259; 514/885
(58) Field of Search ....................................... 514/259, 885

(56) References Cited

U.S. PATENT DOCUMENTS

| | | |
|---|---|---|
| 4,343,804 | 8/1982 | Munson et al. . |
| 5,475,105 | 12/1995 | Steiner et al. . |
| 5,480,883 | 1/1996 | Spada et al. . |
| 5,580,870 | 12/1996 | Barker et al. . |
| 5,760,041 * | 6/1998 | Wissner et al. .................. 514/259 |
| 5,891,651 * | 4/1999 | Roche et al. .................... 435/7.21 |

FOREIGN PATENT DOCUMENTS

| | | |
|---|---|---|
| 2148324 | 11/1995 | (CA) . |
| 0520722 | 6/1992 | (EP) . |
| 0566226 | 1/1993 | (EP) . |
| 0602851 | 9/1993 | (EP) . |
| 0635498 | 7/1994 | (EP) . |
| 0787722 | 8/1997 | (EP) . |
| 9515758 | 6/1995 | (WO) . |
| 9519774 | 7/1995 | (WO) . |
| 9519970 | 7/1995 | (WO) . |
| 9521613 | 8/1995 | (WO) . |
| 9523141 | 8/1995 | (WO) . |
| 9524190 | 9/1995 | (WO) . |
| 9609294 | 3/1996 | (WO) . |
| 9615118 | 5/1996 | (WO) . |
| 9738983 | 10/1997 | (WO) . |

OTHER PUBLICATIONS

Ramdas et al., *Archives of Biochemistry and Biophysics*, 323(2), 1995, 237–42.
Fry, D. W. et al., Science, 265:1093–1095 (1994).
Ife, R. J. et al., J. Med. Chem. 35:3413–3422 (1992).
Maguire, M. P. et al., J. Med. Chem. 37:2129–2137 (1994).
Marecki, P. E. et al., Journal of Pharmaceutical Sciences 73:1141–1143 (1984).
Rewcastle, G. W. et al., J. Med. Chem. 38:3482–3487 (1995).
Sarges, R. et al., J. Med. Chem. 36:2828–2830 (1993).
Pellerano, C., et al., IL FARMACO 45(3):269–284 (1990).
Savini, L.., et al., IL FARMACO 48(6):805–825 (1993).
Dolle, R. E., et al., J. Med. Chem. 37:2627–2629 (1994).
Bridges, A. J., et al., J. Med. Chem. 39:267–276 (1996).
Avner, E.D. et al., J. Amer. Soc. Nephrology, 6(3), 1995, p. 690.
Wilson, P.D. et al., Eur. J. Cell. Biol., 61(1), Jun. 1993, pp. 131–138.
Wilson, P.D., Am. J. Kidney Dis., 17(6), Jun. 1991, pp. 634–637.

* cited by examiner

*Primary Examiner*—Frederick Krass
(74) *Attorney, Agent, or Firm*—John W. Hogan, Jr.

(57) ABSTRACT

This invention provides a method of treating or inhibiting colonic polyps in a mammal in need thereof which comprises administering to said mammal a compound having the formula wherein:

X is phenyl which is optionally substituted;

R and $R_1$ are each, independently, hydrogen, halogen, alkyl, alkoxy, hydroxy, or trifluoromethyl;

$R_2$ is hydrogen, alkyl, alkoxy, hydroxy, trifluoromethyl;

Y is a radical selected from the group consisting of and $R_3$ is independently hydrogen, alkyl, carboxy, carboalkoxy, phenyl, or carboalkyl;

n=2–4;

or a pharmaceutically acceptable salt thereof, with the proviso that each $R_3$ of Y may be the same or different.

14 Claims, No Drawings

METHOD OF TREATING OR INHIBITING COLONIC POLYPS

This application claims the benefit of U.S. Provisional Application No. 60/112,025 filed Nov. 6, 1997 which was converted from U.S. patent application Ser. No. 08/965,084, filed Nov. 6, 1997, pursuant to a petition filed under 37 C.F.R. 1.53(c)(2)(i) on Apr. 13, 1998.

This invention relates to the use of certain quinazoline compounds in the treatment and inhibition of colonic polyps.

Colonic Polyps occur in both a familial pattern (Familial Adenomatous Polyps (FAP) and sporadically. FAP afflicts approximately 25,000 patients in the US; while it is estimated that sporadic adenomatous polyps (SAP) occur in approximately 2 million people per year in the US alone. All these patients are at risk for developing adenocarcinoma of the colon. In the case of FAP, that risk is virtually 100% and these patients usually undergo a colectomy at an early age. Patients with sporadic polyps are treated with polypectomy and require periodic colonoscopic examination because of their inherent risk of developing recurrent polyps. In fact, parents and siblings of these patients are also at increased risk for developing colorectal cancer.

The genetic basis for FAP has been linked to the presence of mutations in the APC gene. Similar APC mutations have been found in patients with sporadic polyps. Biochemically, the APC mutation occurs in conjunction with the increased expression of cyclooxygenase enzymes, particularly COX-2. These enzymes are essential for the production of prostenoids, (prostaglandin's; (PG's)) that mediate a number of functions in the bowel including motility, vascular tone, angiogenesis and mucosal protection. PG's are also purported to discourage apoptosis and this is proposed as an explanation for polyp formation.

The therapy of FAP and SAP has focused on inhibiting COX enzymes. Considerable evidence exists for the efficacy of COX inhibitors in reducing polyp formation. These COX inhibitors are predominantly NSAID's such as clinoril, sulindac, piroxicam and etodoloc, all of which appear to be equivalent in their action. A major problem with NSAID therapy has been the development of serious side effects including peptic ulceration, and cholestatic hepatitis and renal papillary necrosis. Long term therapy with NSAIDs for the treatment of polyps is therefore considered to be impractical.

It has recently been proposed that the activation and overexpression of COX-2 in adenomatous polyps is due to activation of the epidermal growth factor receptor (EGFR). EGFR stimulation by one of it's ligands—amphiregulin (AR), induces the nuclear targeting of COX-2, release of PG's and subsequent mitogenesis, in polarized colonic epithelial cells. COX-2 inhibitors have been shown to prevent this series of events.

DESCRIPTION OF THE INVENTION

This invention provides a method of treating or inhibiting colonic polyps in a mammal in need thereof which comprises administering to said mammal a compound of formula 1:

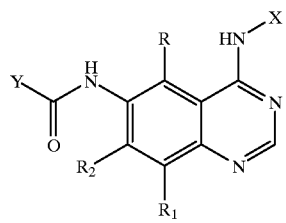

wherein:

X is phenyl optionally substituted with one or more substituents selected from the group consisting of halogen, alkyl of 1–6 carbon atoms, alkoxy of 1–6 carbon atoms, hydroxy, trifluoromethyl, cyano, nitro, carboxy, carboalkoxy of 2–7 carbon atoms, carboalkyl of 2–7 carbon atoms, amino, and alkanoylamino of 1–6 carbon atoms;

R and $R_1$ are each, independently, hydrogen, halogen, alkyl of 1–6 carbon atoms, alkoxy of 1–6 carbon atoms, hydroxy, or trifluoromethyl;

$R_2$ is hydrogen, alkyl of 1–6 carbon atoms, alkoxy of 1–6 carbon atoms, hydroxy, trifluoromethyl;

Y is a radical selected from the group consisting of

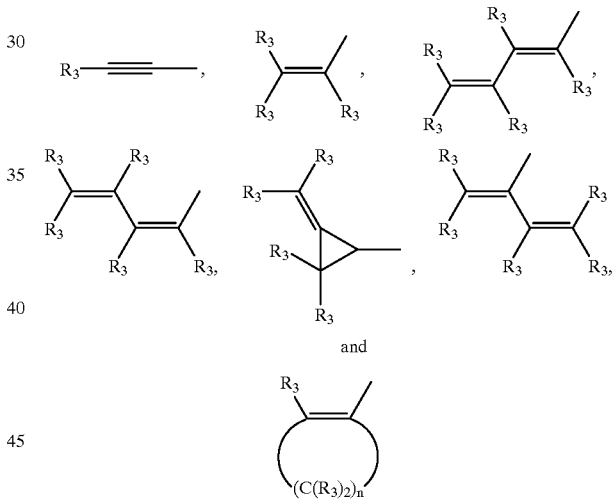

$R_3$ is independently hydrogen, alkyl of 1–6 carbon atoms, carboxy, carboalkoxy of 1–6 carbon atoms, phenyl, or carboalkyl of 2–7 carbon atoms;

n=2–4;

or a pharmaceutically acceptable salt thereof, with the proviso that each $R_3$ of Y may be the same or different.

The pharmaceutically acceptable salts are those derived from such organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

The alkyl portion of the alkyl, alkoxy, carboalkoxy, carboalkyl, and alkanoylamino substituents include both straight chain as well as branched carbon chains. Carboxy is defined as a —$CO_2H$ radical. Carboalkoxy of 2–7 carbon atoms is defined as a —$CO_2R''$ radical, where R'' is an alkyl radical of 1–6 carbon atoms. Carboalkyl is defined as a —COR'' radical, where R'' is an alkyl radical of 1–6 carbon atoms. When X is substituted, it is preferred that it is mono-, di-, or tri-substituted, with monosubstituted being most preferred. When a compound of this invention contains an assymetric center, this invention covers the individual R and S entantiomers as well as the racemate with respect to such compound.

Of the compounds of this invention, preferred members include those in which R, $R^1$, and $R^2$ are hydrogen; and those in which R, $R^1$, and $R^2$ are hydrogen and X is either unsubstituted or monosubstituted with halogen or alkyl of 1–6 carbon atoms.

The preparation of the compounds of this invention encompassed by Formula 9 is described below in Flowsheet A where R, $R_1$, $R_2$, $R_3$, X, and n are defined and $R_4$ is alkyl of 1–6 carbon atoms (preferably isobutyl). Y' is a radical selected from the group consisting of:

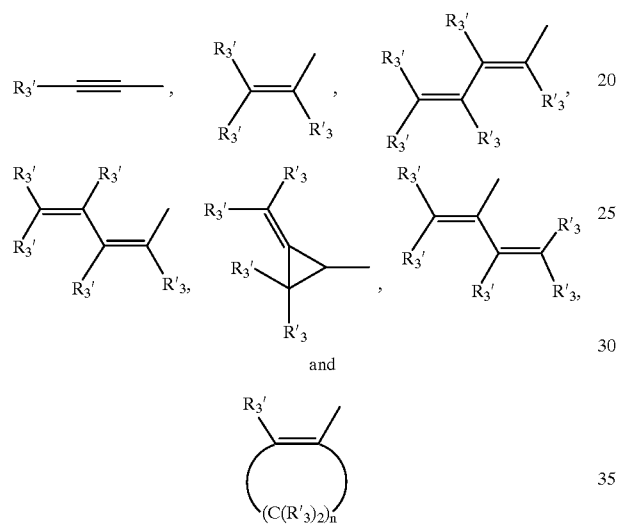

and wherein each $R'_3$ is independently alkyl of 1–6 carbon atoms, carboxy, carboalkoxy of 1–6 carbon atoms, phenyl, or carboalkyl of 2–7 carbon atoms. According to the sequence of reaction outlined in flowsheet A, a 5-nitro-anthranilonitrile of Formula 2 is heated at about 100° C. with or without solvent containing an excess of dimethylformamide dimethyl acetal to furnish an amidine of Formula 3. Heating a solution of amidine 3 and the aniline 4 in acetic acid for 1 to 5 hours gives the 6-nitro-4-anilinoquinazolines of Formula 5. Reduction of the nitro group of 5 using a reducing agent such as iron in an acetic acid-alcohol mixture at elevated temperature gives the 6-amino-4-anilinoquinazolines of Formula 6. Acylation of 6 with either an acid chloride of Formula 7 or a mixed anhydride of Formula 8 (which is prepared from the corresponding carboxylic acid) in an inert solvent such as tetrahydrofuran (THF) in the presence of an organic base such as pyridine or triethylamine gives the compounds of this invention represented by Formula 9. In those cases where 7 or 8 have an asymmetric carbon atom, they can be used as the racemate or as the individual R or S entantiomers in which case the compounds of this invention will be in the racemic or R and S optically active forms, respectively. The 5-nitro-anthranilonitriles of Formula 2 needed to prepare the compounds of this invention are either already known to the art or can be prepared by procedures known in the art as detailed in the following references: Baudet, Recl.Trav.Chim.Pays-Bas, 43, 710 (1924); Hartmans, Recl.Trav.Chim.Pays-Bas, 65, 468, 469 (1946); Taylor et al., J.Amer.Chem.Soc., 82, 6058,6063 (1960); Taylor et al., J.Amer.Chem.Soc., 82, 3152,3154 (1960); Deshpande; Seshadri, Indian J.Chem., 11 , 538 (1973); Katritzky, Alan R.; Laurenzo, Kathleen S., J.Org.Chem., 51 (1986); Niclas, Hans-Joachim; Bohle, Matthias; Rick, Jens-Detlev; Zeuner, Frank; Zoelch, Lothar, Z.Chem., 25(4), 137–138 (1985).

FLOWSHEET A

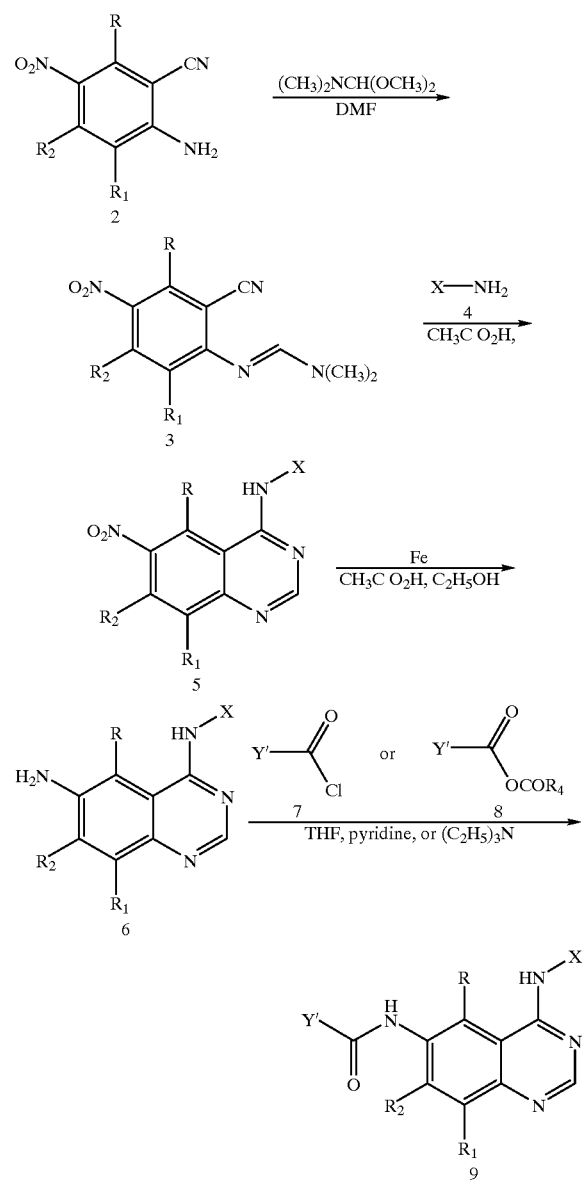

The preparation of the compounds of this invention encompassed by Formula 12 is described below in Flowsheet B wherein R, $R_1$, $R_2$, X, and n are described above. Each $R_5$ is independently hydrogen, phenyl, or alkyl of 1–6 carbon atoms. According to the reaction outlined in Flowsheet B, the 6-amino-4-anilinoquinazolines of Formula 10 (prepared as in Flowsheet A) are acylated with a cyclic anhydride of Formula 11 in an inert solvent such as tetrahydrofuran in the presence of a basic catalyst such as pyridine or triethylamine.

FLOWSHEET B

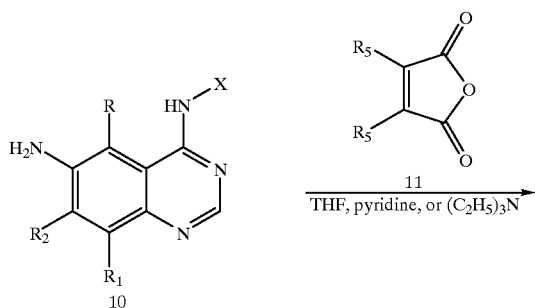

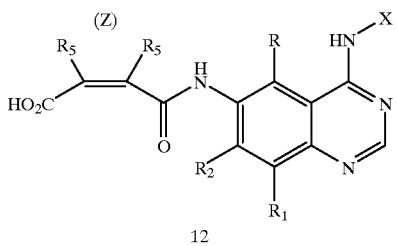

Representative compounds of this invention were evaluated in several standard pharmacological test procedures that showed that the compounds of this invention possess significant activity as inhibitors of protein tyrosine kinases, and are antiproliferative agents. Based on the activity shown in the standard pharmacological test procedures, the compounds of this invention are therefore useful as antineoplastic agents. The test procedures used and results obtained are shown below.

The preparation of the compounds of this invention encompassed by Formula 19 is described below in Flowsheet C wherein Y', $R_4$, and X are described above. According to the reactions outlined in Flowsheet C, 4-choro-6-nitroquinazoline, 13, (Morley, JS. and Simpson, *J. Chem. Soc.*, 360 (1948)) is reduced to 6-amino-4-chloroquinazoline, 14, using a reducing agent such as sodium hydrosulfite in a two phase system consisting of tetrahydrofuran and water in the presence of a small amount of phase transfer catalyst. Acylation of 14 with either an acid chloride of Formula 15 or a mixed anhydride of Formula 16 (which is prepared from the corresponding carboxylic acid) in an inert solvent such as tetrahydrofuran (THF) in the presence of an organic base such as pyridine or N-methyl morpholine gives the compounds of Formula 17. In those cases where 15 or 16 have an asymmetric carbon atom, they can be used as the racemate or as the individual R or S entantiomers in which case the compounds of this invention will be in the racemic or R and S optically active forms, respectively. Heating a compound of Formula 17 with an aniline of Formula 18, in a inert solvent such as isopropanol, gives the compounds of this invention represented by Formula 19.

FLOWSHEET C

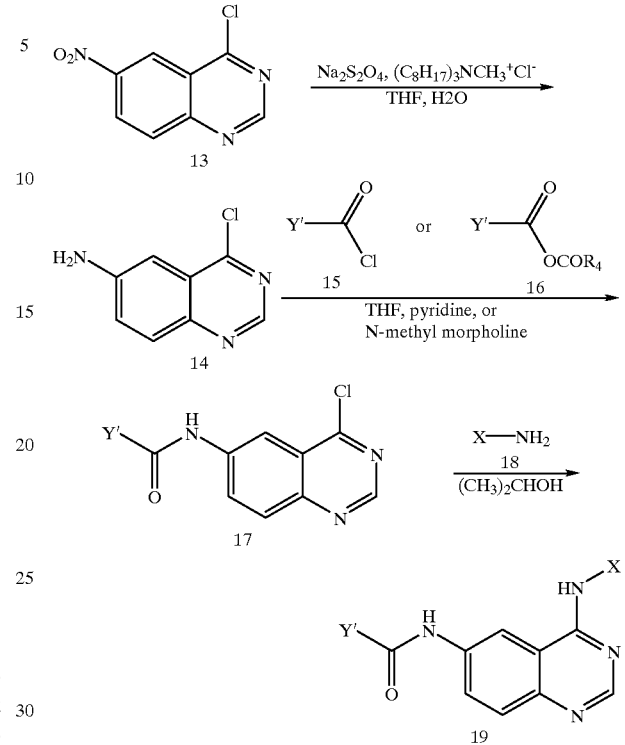

The preparation of the compounds of this invention encompassed by Formula 26 is described below in Flowsheet D wherein Y', $R_4$, and X are described above. According to the reactions outlined in Flowsheet D, the nitro group of 20 (prepared as in Flowsheet A) is reduced to the corresponding amino compound 21 using a palladium catalyst and a source of hydrogen which can be hydrogen itself or cyclohexene. Acylation of 21 with either an acid chloride of Formula 22 or a mixed anhydride of Formula 23 (which is prepared from the corresponding carboxylic acid) in an inert solvent such as tetrahydrofuran (THF) in the presence of an organic base such as pyridine or N-methyl morpholine gives the compounds of Formula 24. In those cases where 22 or 23 have an asymmetric carbon atom, they can be used as the racemate or as the individual R or S entantiomers in which case the compounds of this invention will be in the racemic or R and S optically active forms, respectively. Heating a compound of Formula 24 with an aniline of Formula 25, in a inert solvent such as acetic acid gives the compounds of this invention represented by Formula 26.

FLOWSHEET D

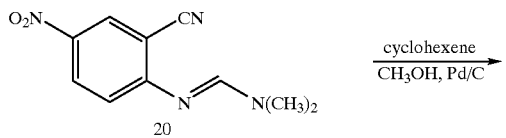

-continued

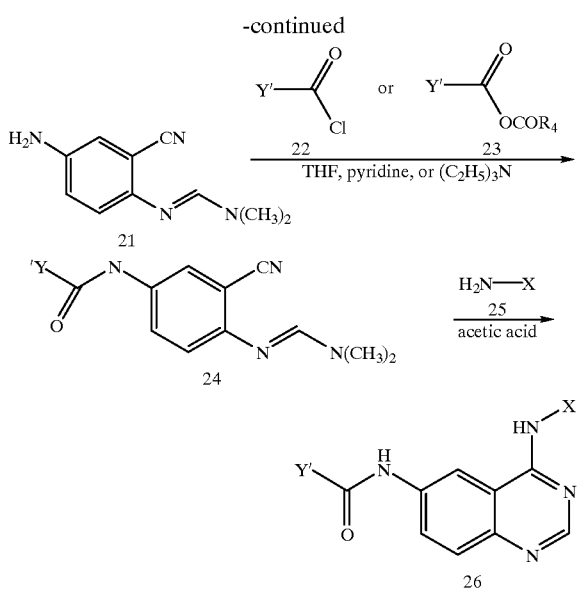

The ability of the compounds of this invention to treat or inhibit colonic polyps was demonstrated in an in vivo standard pharmacological test procedure as described below. The compound of Example 9 was evaluated in this procedure, which emulates familial adenomatous polyps (FAP) in humans, as a representative compound of this invention. The Min mouse used in this test procedure, currently the best available model for FAP, is a strain which has lost both copies of the APC gene. These animals develop multiple intestinal polyps (Adenomas) that ultimately progress to form adenocarcinomas. The polyps that develop in Min mice express EGFR and have activated COX-2. NSAID's such as sulindac and etodoloc can reduce (but not eradicate) intestinal polyp formulation in these animals indicating that COX-2 and the ultimate production of PG's is likely responsible for these effects. The following briefly describes the procedure used and the results obtained in this standard pharmacological test procedure.

The compound of Example 9 was blended with a standard murine chow and animals were given ad libitum access to the food. Based on estimated food consumption, the compound of Example 9 was added at a concentration commensurate with animals ingesting 20 mg/kg/day. At day 30, 4 treated +4 control (chow alone) animals were sacrificed and assessed for polyp number. All control animals had greater than 30 polyps in their bowel, while the treated animals had none. Identical results were observed at 60 days—when 15 animals/group were assessed. The control animals had greater than 30 (larger) polyps while the treated animals had none.

These data demonstrate that the compounds of this invention effectively inhibit polyp formation in animals having mutations in their APC genes. Based on the results obtained in this standard pharmacological test procedure, the compounds of this invention are useful in treating or inhibiting the formation of colonic polyps.

The compounds of this invention may formulated neat or may be combined with one or more pharmaceutically acceptable carriers for administration. For example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solution or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 1000 mg/kg of animal body weight, optionally given in divided doses two to four times a day, or in sustained release form. For most large mammals the total daily dosage is from about 1 to 1000 mg, preferably from about 2 to 500 mg. Dosage forms suitable for internal use comprise from about 0.5 to 1000 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

In some cases it may be desirable to administer the compounds directly to the airways in the form of an aerosol.

These active compounds may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The preparation of representative examples of the compounds of this invention is described below.

EXAMPLE 1

N'-(2-Cyano-4-nitrophenyl)-N,N-dimethylformamidine

A 40.8 g portion of 5-nitro-anthranilonitrile and 40 ml of N, N-dimethylformamide dimethyl acetal were heated on a steam bath for 2 hours. The solvents were removed at reduced pressure and the residue was taken up in methylene chloride. After passing this solution through Magnesol the solvent was removed. After washing with ether 50.8 g of N'-(2-cyano-4-nitrophenyl)-N,N-dimethylformamidine was obtained.

EXAMPLE 2

N-(3-Bromophenyl)-6-nitro4-quinazolinamine

A solution of 23.74 ml of 3-bromo aniline and 40.5 g N'-(2-cyano-4-nitrophenyl)-N,N-dimethylformamidine in 100 ml of glacial acetic acid was stirred and heated in an oil bath at 148° C. for 1.5 hours. On cooling, filtration of the resulting solid gives a quantitative yield of N-(3-bromophenyl)-6-nitro4-quinazolinamine: mp=267–270° C.; mass spectrum (m/e): 345.

EXAMPLE 3

N-(3-Bromophenyl)-4.6-quinazolindiamine

A mixture of 34.5 g of N-(3-bromophenyl)-6-nitro-4-quinazolinamine and 16.8 g of iron powder in 150 ml of ethanol and 150 ml of glacial acetic acid was heated in an oil bath at 120° C. for 2 hours. After filtration of the solid, solid sodium carbonate was added to the filtrate giving a solid. This was filtered, and the solid was extracted with methanol. The extracts were treated with charcoal and evaporated to a solid. After washing the solid with ether 27.5 g of N-(3-bromophenyl)-4,6-quinazolindiamine was obtained: mass spectrum (m/e): 315.

EXAMPLE 4

4-[[4-[(3-Bromophenyl)amino]-6-quinazolinyl] amino]-4-oxo-(Z)-2-butenoic acid

A 15 ml portion of pyridine was added to 1.6 g of N-(3-bromophenyl)-4,6-quinazolindiamine and 0.6 g of maleic anhydride. After stirring overnight, the solvents were removed on the rotary evaporator. The solid was taken up in about 400 ml of hot ethanol and the insoluble material filtered to give 0.33 g of 4-[[4-[(3-Bromophenyl)amino]-6-quinazolinyl]amino]-4-oxo-(Z)-2-butenoic acid: mass spectrum (m/e): M+H 413, 415.

EXAMPLE 5

4-[[4-[(3-Bromophenyl)amino]-6-quinazolinyl] amino]-4-oxo-(E)-2-butenoic acid, ethyl ester A solution of N-(3-bromophenyl)-4,6-quinazolindiamine in 15 ml of pyridine was cooled in an ice bath and a solution of 1.22 g of ethyl fumaryl chloride in 10 ml of methylene chloride was added dropwise. After stirring for 1.5 hours, the reaction was allowed to come to room temperature. The solvents were removed at reduced pressure and the residue was treated with water. The red solid was filtered and extracted into hot acetone. After filtration of the insoluble material, the filtrate was concentrated to give 0.45 g of 4-[[4-[(3-Bromophenyl)amino]-6-quinazolinyl]amino]-4-oxo-(E)-2-butenoic acid, ethyl ester: mp=259–263° C., mass spectrum (m/e): M+H 441, 443.

EXAMPLE 6

N-[4-[(3-Bromophenyl)amino]-6-quinazolinyl]-3-methyl-2-butenamide

A solution of 1.58 g of N-(3-bromophenyl)-4,6-quinazolindiamine in 15 ml of pyridine was cooled in an ice bath and a solution of 0.67 ml of 3,3-dimethylacryloyl chloride in 7 ml of ether was added dropwise. After stirring and cooling for 2 hours, the solvents were removed at reduced pressure. The residue was treated with water and the resulting solid was recrystallized from methyl cellusolve to give 0.97 g of N-[4-[(3-bromophenyl)amino]-6-quinazolinyl]-3-methyl-2-butenamide: mp=300–301° C., mass spectrum (m/e): 396, 398.

EXAMPLE 7

N-[4-[(3-Bromophenyl)amino]-6-quinazolinyl]-(E)-2-butenamide

A solution of 1.6 g of N-(3-bromophenyl)-4,6-quinazolindiamine in 15 ml of pyridine was cooled in an ice bath and a solution of 0.57 ml of trans-crotonoyl chloride in 6 ml of ether was added dropwise. After stirring and cooling for 2 hours, the solvents were removed at reduced pressure. The residue was treated with water and the resulting solid recrystallized from n-butanol to give 0.69 g of N-[4-[(3-bromophenyl)amino]-6-quinazolinyl]-(E)-2-butenamide: mp=153–160° C., mass spectrum (m/e): M+H 383, 385.

EXAMPLE 8

N-[4-[(3-Bromophenyl)amino]-6-quinazolinyl]-2-methyl-2-propenamide

A solution of 1.6 g of N-(3-bromophenyl)4,6-quinazolindiamine in 15 ml of pyridine was cooled in an ice bath and a solution of 0.59 ml of methacryoyl chloride in 6 ml of ether was added dropwise. After stirring and cooling for 2 hours, the solvents were removed at reduced pressure. The residue was treated with water and the resulting solid was taken up in n-butanol (warming). Addition of ether to the cooled solution gives 0.44 g of N-[4-[(3-bromophenyl)amino]-6-quinazolinyl]-2-methyl-2-propenamide: mp=40–245° C., mass spectrum (m/e): M+H 383, 385.

EXAMPLE 9

N-[4-[(3-Bromophenyl)amino]-6-quinazolinyl]-2-butynamide

A solution of 0.50 g of 2-butynoic acid in 10 ml of tetrahydrofuran was cooled in an ice bath. A 0.79 ml portion of isobutyl chloroformate followed by a 0.66 ml portion of N-methyl morpholine were added. After about 1 minute a solution of 1.6 g of N-(3-bromophenyl)-4,6-quinazolindiamine in 10 ml of pyridine was added. The reaction was allowed to come to room temperature and stir overnight. The solvents were removed at reduced pressure and the solid was recrystallized from n-butanol to give 1.07 g of N-[4-[(3-bromophenyl)amino]-6-quinazolinyl)-2-butynamide: mass spectrum (m/e): 381, 383.

EXAMPLE 10

4-[[4-[(3-Bromophenyl)amino]6-quinazolinyl] amino]-4-oxo-(E)-2-butenoic acid

A 2.5 ml portion of 10 N aqueous sodium hydroxide was added to 2.3 g of 4-[[4-[(3-bromophenyl) amino]-6- quinazolinyl]amino]-4-oxo-(E)-2-butenoic acid ethyl ester (Example 5) in 25 ml of ethanol. After stirring for an hour, 2.1 ml of concentrated hydrochloric acid was added, and the reaction was stirred an additional 2 hours. The resulting solid was recrystallized from n-butanol to give 0.97 g of 4-[[4-[(3-Bromophenyl)amino]-6-quinazolinyl]amino]-4-oxo-(E)-2-butenoic acid: mass spectrum (m/e): M+H 413.

EXAMPLE 11

N-[4-[(3-Bromophenyl)amino]-6-quinazolinyl]-2,4-hexadienamide

A solution of 0.67g of 2,4-hexadienoic acid in 10 ml of tetrahydrofuran was cooled in an ice bath. A 0.79 ml portion of isobutyl chloroformate followed by a 0.66 ml portion of N-methyl morpholine were added. After about 1 minute a solution of 1.6 g of N-(3-bromophenyl)-4,6-quinazolindiamine in 10 ml of pyridine was added. The reaction was allowed to come to room temperature and stir overnight. The solvents were removed at reduced pressure and the solid was recrystallized to give 1.0 g of N-[4-[(3-bromophenyl)amino]-6-quinazolinyl]-2,4-hexadienamide: mp=258–260° C.

EXAMPLE 12

N-[4-[(3-Bromophenyl)amino]-6-quinazolinyl]-2-cyclopenteneamide

A solution of 0.43 g of 2-cyclopentenoic acid in 5 ml of tetrahydrofuran was cooled in an ice bath. A 0.49 ml portion of isobutyl chloroformate followed by a 0.41 ml portion of N-methyl morpholine were added. After about 1 minute a solution of 1.0 g of N-(3-bromophenyl)-4,6-quinazolindiamine in 10 ml of pyridine was added. The reaction was allowed to come to room temperature and stir overnight. Another 0.5 equivalents of mixed anhydride was added. The mixture was stirred for 5 hours. The solvents were removed at reduced pressure and the solid was purified by chromatography on silica gel to give 0.30 g of N-[4-[(3-bromophenyl)amino]-6-quinazolinyl]-2-cyclopenteneamide: mass spectrum (m/e): 409 (M+H, EI).

EXAMPLE 13

N-[4-[(3-Bromophenyl)amino]-6-quinazolinyl]-2-propenamide

A solution of 2.0 g of N-(3-bromophenyl)-4,6-quinazolindiamine in 10 ml of pyridine was cooled in an ice bath and a solution of 0.61 ml of acryoyl chloride in 30 ml of ether was added dropwise at 0° C. After stirring at room temperature for 3.5 hours, the solvents were removed at reduced pressure. The residue was purified by chromatography to give 0.2 g of N-[4-[(3-bromophenyl)amino]-6-quinazolinyl]-2-propenamide: mass spectrum (m/e): M+H 369.

EXAMPLE 14

N-[4-[(3-Bromophenyl)amino]-6-quinazolinyl1-(3-phenyl-2-propynamide)

A solution of 0.93 g of 3-phenyl-2-propynoic acid in 10 ml of tetrahydrofuran was cooled in an ice bath. A 0.82 ml portion of isobutyl chloroformate followed by a 0.69 ml portion of N-methyl morpholine were added. After about 1 minute a solution of 1.0 g of N-(3-bromophenyl)4,6-quinazolindiamine in 7 ml of pyridine was added. The reaction at 0° C. for 1 hr.. The solvents were removed at reduced pressure and the solid was purified by chromatography on silica gel to give 0.01 g of N-[4-[(3-bromophenyl)amino]-6-quinazolinyl]-(3-phenyl-2-propynamide): mass spectrum (m/e): 443.2, 445.2 (M+H, electrospray).

EXAMPLE 15

6-amino4-chloroquinazoline

A mixture consisting of 3.25 g of 4-chloro-6-nitroquinazoline, 10.8 g of sodium hydrosulfite, and 0.3 g of the phase transfer catalyst $(C_8H_{17})_3NCH_3)_3NCH_3{}^+Cl^-$ in 97 ml of tetrahydrofuran and 32 ml of water was stirred rapidly for 2 hours. The mixture was diluted with ether and the organic layer was separated. The organic solution was washed with brine and then dried over magnesium sulfate. The solution was passed through a small column of silica gel. The solvent was removed at 30° C. at reduced pressure giving 6amino-4-chloroquinazoline which is used in the next step without additional purification.

EXAMPLE 16

[4-chloro-6-quinazolinyl]-2-butynamide

A solution of 1.64 g of 2-butynoic acid in 46 ml of tetrahydrofuran was cooled in an ice bath. A 2.34 ml portion of isobutyl chloroformate followed by a 4.13 ml portion of N-methyl morpholine were added. After about 10 minutes, this was poured into a solution of 6-amino-4-chloroquinazoline in 46 mnl tetrahydrofuran. This mixture was stirred at room temperature for 2 hours. The mixture was poured into a mixture of brine and saturated sodium bicarbonate and extracted with ether. The ether solution was dried over magnesium sulfate and filtered. The solvent was removed giving ]4-chloro-6-quinazolinyl]-2-butynamide as colored oil that was used in the next step without additional purification.

EXAMPLE 17

N-[4-[(3-Bromophenyl)amino]-6-quinazolinyl]-2-butynamide

A solution consisting of 1.76 g of [4-chloro-6-quinazolinyl]-2-butynamide and 1.23 g of 3-bromo aniline was refluxed under an inert atmosphere in 23 ml of isopropanol for 40 minutes. The mixture was cooled to room temperature and 200 ml of ether was added giving 0.4 g of N-[4-[(3-bromophenyl)amino]-6-quinazolinyl]-2-butynamide as the hydrochloride salt. Neutralizing with sodium bicarbonate solution, extracting with ethyl acetate, removal of the solvent, and recyrstallization from 1-butanol gives N-[4-[(3-bromophenyl)amino]-6-quinazolinyl]-2-butynamide as the free base.

EXAMPLE 18

N'-(4-Amino-2-cyanophenyl)-N,N-dimethylformamidine

A solution of 6.0 g (27.5 mmol) of N'-(2-cyano-4-nitrophenyl)-N,N-dimethylformamidine, 33.9 g (41.8 ml, 412.4 mmol) of cyclohexene, and 0.6 g of 10% Pd/C in 360 ml of methanol was refluxed for 4 hrs. The hot mixture was filtered through Celite. Solvent was removed and the residue was recrystallized from chloroform-carbon tetrachloride giving 4.9 g (95%) of the tidle compound as a light gray crystalline solid. mass spectrum (m/e): 188.9 (M+H, electrospray).

EXAMPLE 19

N-[3-Cyano-4-[[(dimethylamino)methylene]amino] phenyl]-2-butynamide

To a solution of 2.01 g (23.9 mmol) of 2-butynoic acid and 2.9 ml (22.3 mmol) isobutyl chloroformate in 30 ml tetrahydrofuran was stirred at 0° C. under nitrogen as 2.42 g (2.63 ml, 22.3 mmol) of N-methyl morpholine was added over 3 min. After stirring for 15 min., a solution of N'-(4-amino-2-cyanophenyl)-N,N-dimethylformamidine and 1.6 g (1.75 ml, 15.9 mmol) of N-methyl morpholine in 25 ml tetrahydrofuran was added over 4 min. The mixture was stirred 30 min. at 0° C. and 30 min. at room temperature. The mixture was diluted with 70 ml of ethyl acetate and poured into a mixture of brine and saturated sodium bicarbonate. The organic layer was dried ($MgSO_4$) and filtered through a pad of silica gel. The solvent was removed and the residue was stirred with 50 ml of ether. The suspended solid was collected to give 3.61 g (89%) of an off-white solid. mass spectrum (m/e): 255.0 (M+H, electrospray).

EXAMPLE 20

N-[4-[(3-Bromophenyl)amino]-6-quinazolinyl]-2-butynamide

A solution of 3.0 g (11.8 mmol) of N-[3-cyano-4-[[(dimethylamino)methylene]amino]phenyl]-2-butynamide and 2.23 g (12.98 mmol) of 3-bromo aniline in 18 ml of acetic acid was refluxed gently with stirring under nitrogen for 1 hr 15 min.. The mixture was cooled in an ice bath and a solid mass formed. The solid was collected by filtration and washed with ether-acetonitrile 1:1 to give a yellow solid which was recrystallized from ethanol giving 2.51 g of N-[4-[(3-bromophenyl)amino]-6-quinazolinyl]-2-butynamide: mass spectrum (m/e): 381, 383.

What is claimed is:

1. A method of treating or inhibiting colonic polyps in a mammal in need thereof which comprises administering to said mammal a compound of the formula

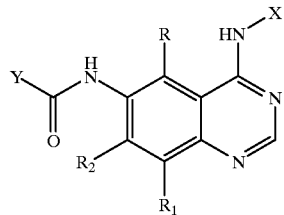

wherein:
X is phenyl optionally substituted with one or more substituents selected from the group consisting of halogen, alkyl of 1–6 carbon atoms, alkoxy of 1–6 carbon atoms, hydroxy, trifluoromethyl, cyano, nitro, carboxy, carboalkoxy of 2–7 carbon atoms, carboalkyl of 2–7 carbon atoms, amino, and alkanoylamino of 1–6 carbon atoms;

R and $R_1$ are each, independently, hydrogen, halogen, alkyl of 1–6 carbon atoms, alkoxy of 1–6 carbon atoms, hydroxy, or trifluoromethyl;

$R_2$ is hydrogen, alkyl of 1–6 carbon atoms, alkoxy of 1–6 carbon atoms, hydroxy, trifluoromethyl;

Y is a radical selected from the group consisting of

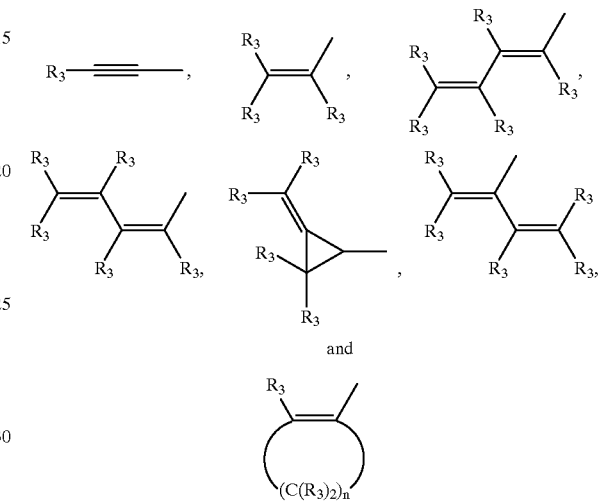

and $R_3$ is independently hydrogen, alkyl of 1–6 carbon atoms, carboxy, carboalkoxy of 1–6 carbon atoms, phenyl, or carboalkyl of 2–7 carbon atoms;

n=2–4;

or a pharmaceutically acceptable salt thereof, with the proviso that each $R_3$ of Y may be the same or different.

2. The method according to claim 1 wherein R, $R_1$, and $R_2$ are hydrogen or a pharmaceutically acceptable salt thereof.

3. The method according to claim 2 wherein X is unsubstituted or substituted with halogen or alkyl of 1–6 carbon atoms.

4. The method according to claim 1 in which N-[4-[(3-Bromophenyl)amino]-6-quinazolinyl]-2-butynamide or a pharmaceutically acceptable salt thereof is administered.

5. The method according to claim 1 in which N-[4-[(3-Bromophenyl)amino]-6-quinazolinyl]-2-methyl-2-propenamide or a pharmaceutically acceptable salt thereof is administered.

6. The method according to claim 1 in which N-[4-[(3-Bromophenyl)amino]-6-quinazolinyl]-2,4-hexadienamide or a pharmaceutically acceptable salt thereof is administered.

7. The method according to claim 1 in which N-[4-[(3-Bromophenyl)amino]-6-quinazolinyl]-(E)-2-butenamide or a pharmaceutically acceptable salt thereof is administered.

8. The method according to claim 1 in which N-[4-[(3-Bromophenyl)amino]-6-quinazolinyl]-3-methyl-2-butynamide or a pharmaceutically acceptable salt thereof is administered.

9. The method according to claim 1 in which 4-[[4-[(3-Bromophenyl)amino]-6-quinazolinyl]amino]-4-oxo-(Z)-2-butenoic acid or a pharmaceutically acceptable salt thereof is administered.

10. The method according to claim 1 in which 4-[[4-[(3-Bromophenyl)amino]-6-quinazolinyl]amino]-4-oxo-(E)-2-butenoic acid or a pharmaceutically acceptable salt thereof is administered.

11. The method according to claim 1 in which 4-[[4-[(3-Bromophenyl)amino]-6-quinazolinyl]amino]-4-oxo-(E)-2-butenoic acid ethyl ester or a pharmaceutically acceptable salt thereof is administered.

12. The method according to claim 1 in which N-[4-[(3-bromophenyl)amino]-6-quinazolinyl]-2-cyclopentenamide or a pharmaceutically acceptable salt thereof is administered.

13. The method according to claim 1 in which N-[4-[(3-Bromophenyl)amino]-6-quinazolinyl]-2-propenamide or a pharmaceutically acceptable salt thereof is administered.

14. The method according to claim 1 in which N-[4-[(3-bromophenyl)amino]-6-quinazolinyl]-(3-phenyl-2-propynamide) or a pharmaceutically acceptable salt thereof is administered.

* * * * *